United States Patent [19]
Perregaard et al.

[11] Patent Number: 5,462,948
[45] Date of Patent: Oct. 31, 1995

[54] TREATMENT OF ADDICTION TO DRUGS AND SUBSTANCES OF ABUSE

[75] Inventors: Jens K. Perregaard, Jaegerspris, Denmark; Brenda Costall, Bradford, United Kingdom

[73] Assignee: H. Lundbeck A/S, Copenhagen-Valby, Denmark

[21] Appl. No.: 115,450

[22] Filed: Sep. 1, 1993

[30] Foreign Application Priority Data

Mar. 1, 1991 [DK] Denmark ................................ 0363/91

[51] Int. Cl.$^6$ .................................................. A61K 31/445
[52] U.S. Cl. ................... 514/323; 514/227.2; 514/228.8; 514/253; 514/318
[58] Field of Search .............................. 514/227.2, 228.8, 514/253, 318, 323

[56] References Cited

U.S. PATENT DOCUMENTS 4,710,500  12/1987  Perregard ................................ 514/254

FOREIGN PATENT DOCUMENTS

WO90/04387  5/1990  WIPO .

OTHER PUBLICATIONS

Even et al "Metabolic Mechanism of the Auorectic and Leptogenic Effects of the Seratonin Against Fenfluramine" CA 105:72494 (1986).
Peroutka et al "Serotonin Receptor Families" Ann. N.Y. Aca. Sci vol. 600 p. 109 (1990).
Monti et al "Ritanserin Decreases Alcohol Intake" Lancet 337 p. 60 (1991).
Haudley et al "Ritanserin Reduces Morphin and Clonidin Withdrawal" Brit. J. Pharmacology 89 p. 647p (1986).
Meert et al "Evidence for Possible Role of the 5HT2 Antagonist" Ann N.Y. Aca Sci 654 pp. 483–486 (1992).

Primary Examiner—Ceila Chang
Attorney, Agent, or Firm—Darby & Darby

[57] ABSTRACT

1-Aryl-3-(4-1piperidyl)-indole derivatives having general formula (I),

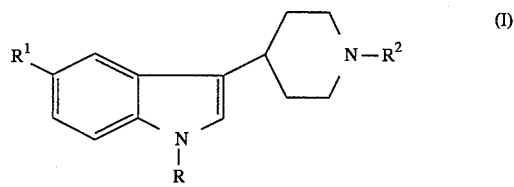

wherein $R^1$ is hydrogen, halogen, alkyl, alkoxy, hydroxy, cyano, nitro, alkylthio, trifluoromethyl, trifluoromethylthio, alkylsulfonyl, amino, alkylamino or dialkylaminio; R is optionally substituted phenyl or a heteroaromatic group; and $R^2$ is hydrogen, cycloalkyl, alkyl or alkenyl, optionally substituted with one or two hydroxy groups, or $R^2$ is a group of formula (IV),

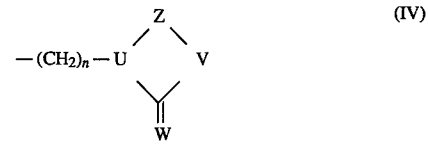

wherein n is an integer of from 2–6; W is O, S or N—$R^3$, wherein $R^3$ is H alkyl or cycloalkyl; U is N or CH, Z is —(CH$_2$)$_m$—, m being 2 or 3, or Z is —CH=CH—, 1,2-phenylene, or —COCH$_2$— or —CSCH$_2$—; V is O,S,CH$_2$, or NR$^4$, wherein R$^4$ is hydrogen, optionally hydroxy substituted alkyl, alkenyl or cycloalkylmethyl; are useful in alleviating, relieving or suppressing withdrawal or abstinence symptons or suppressing the dependency of a drug or a substance of abuse.

3 Claims, 16 Drawing Sheets

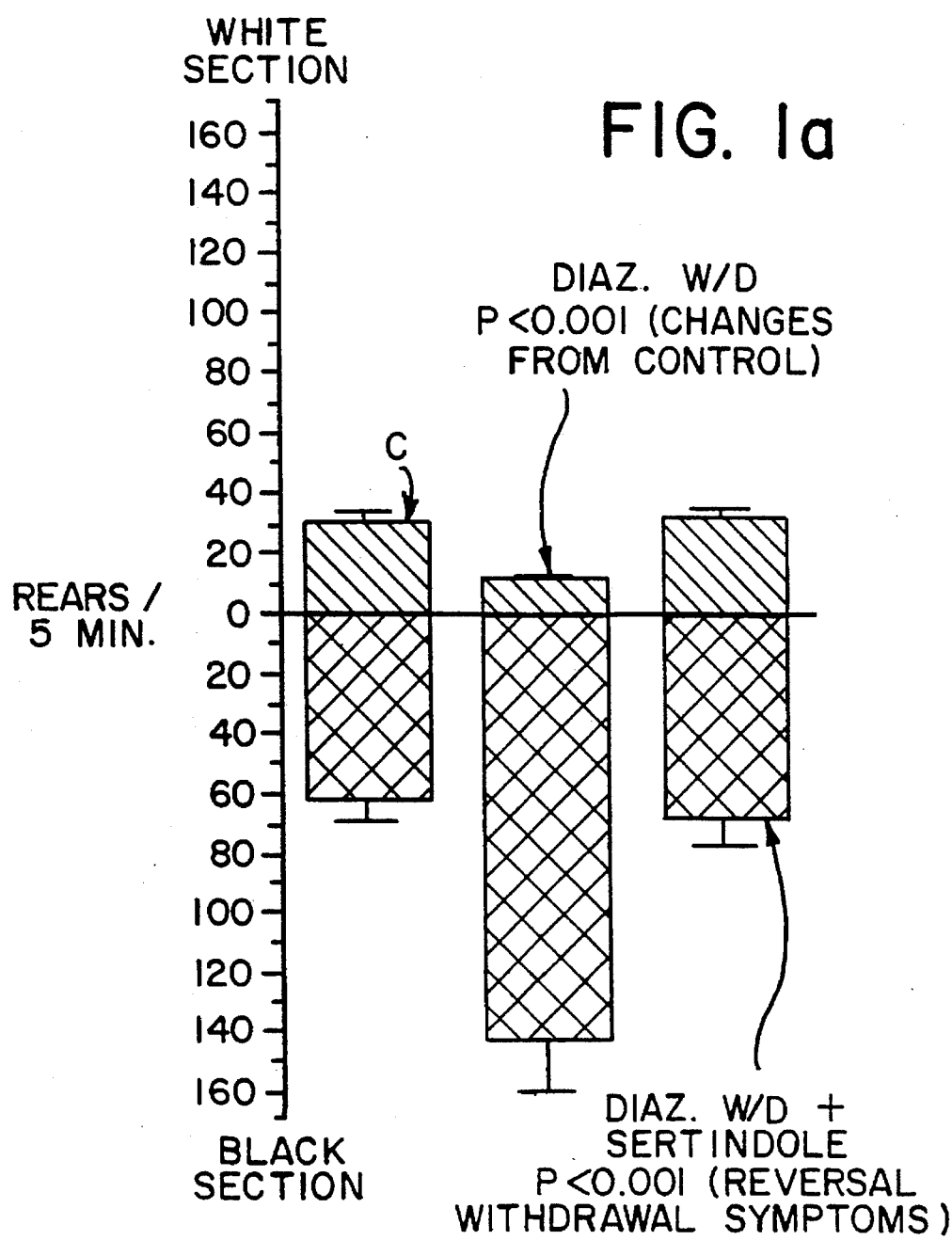

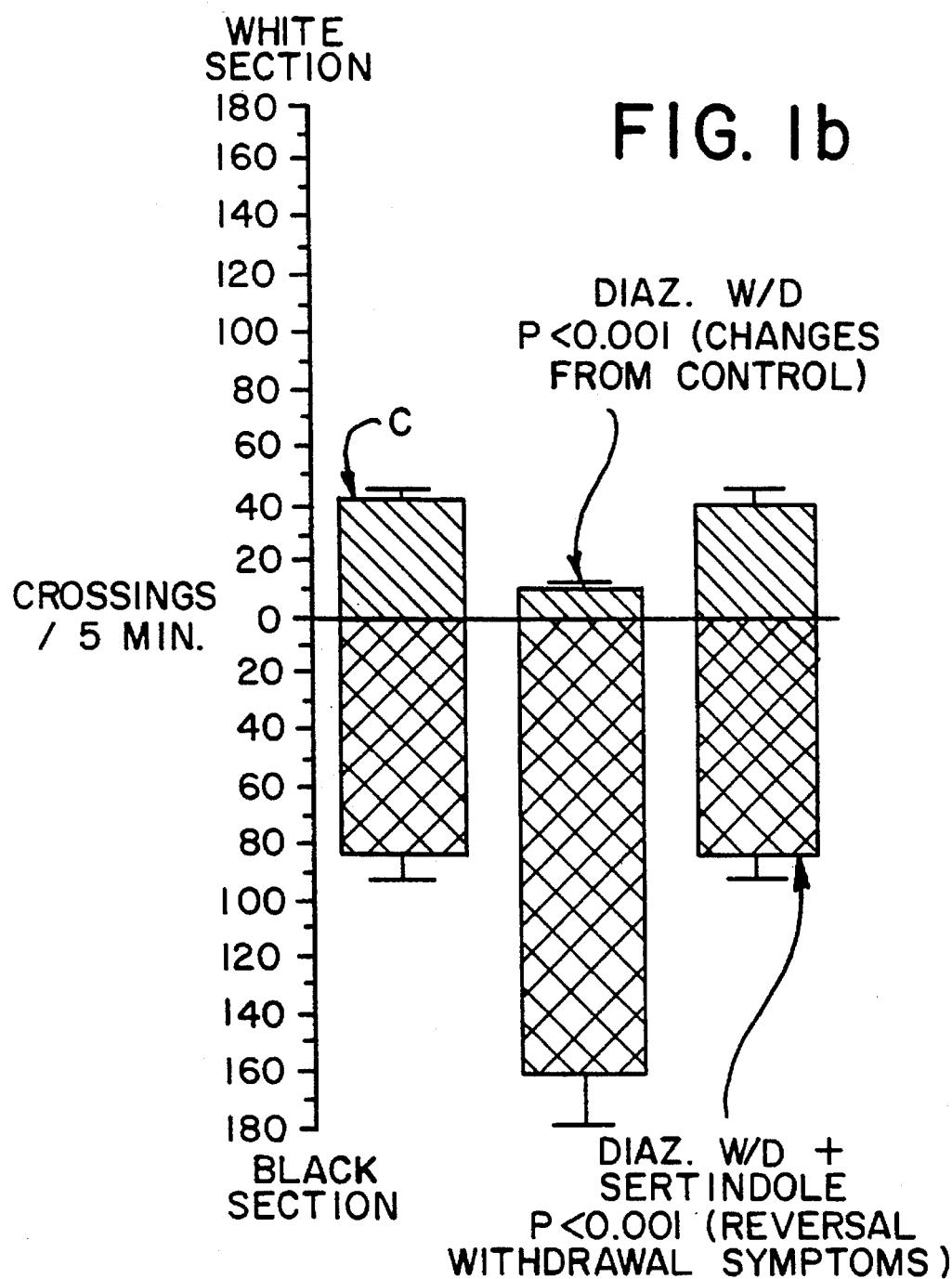

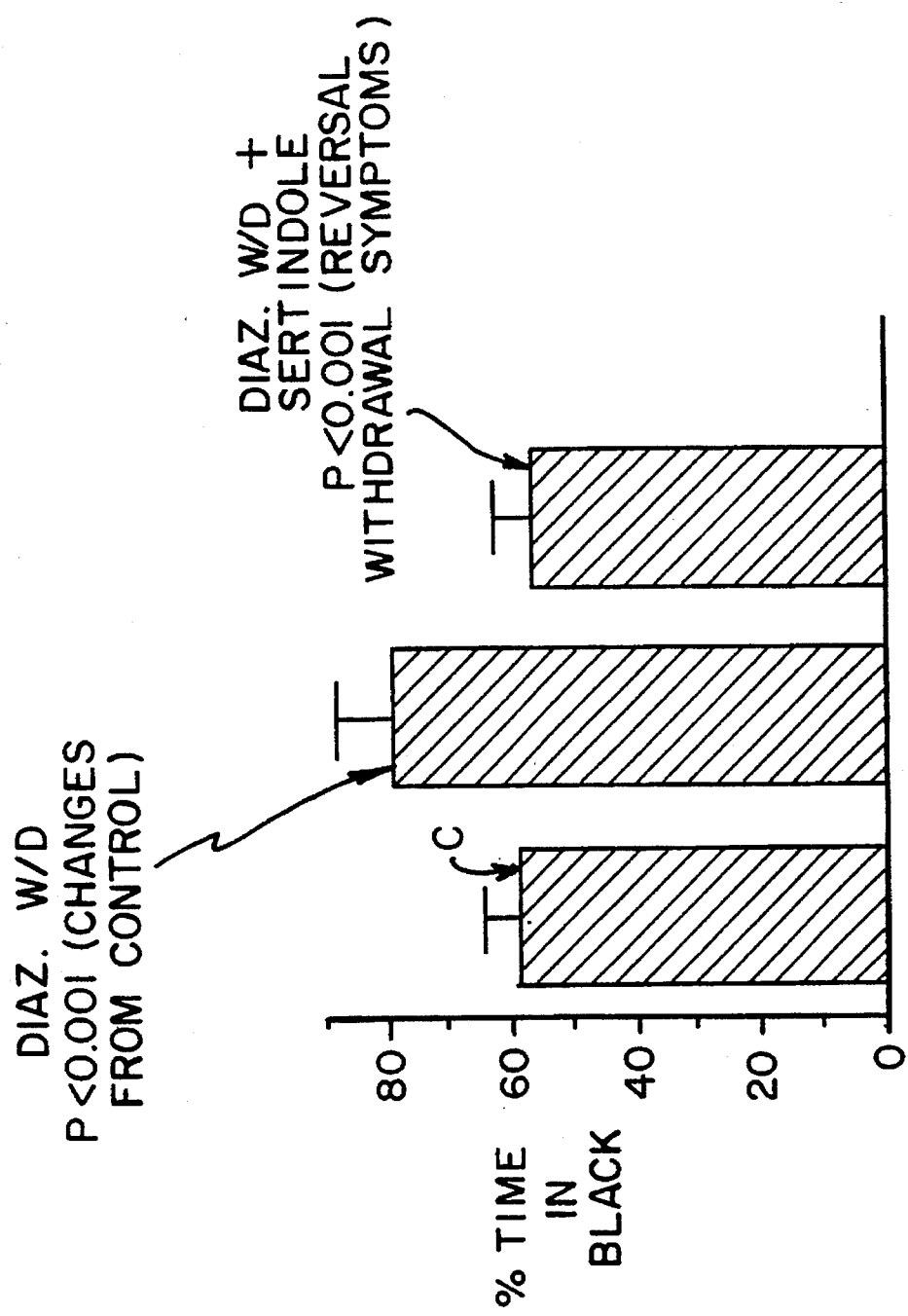

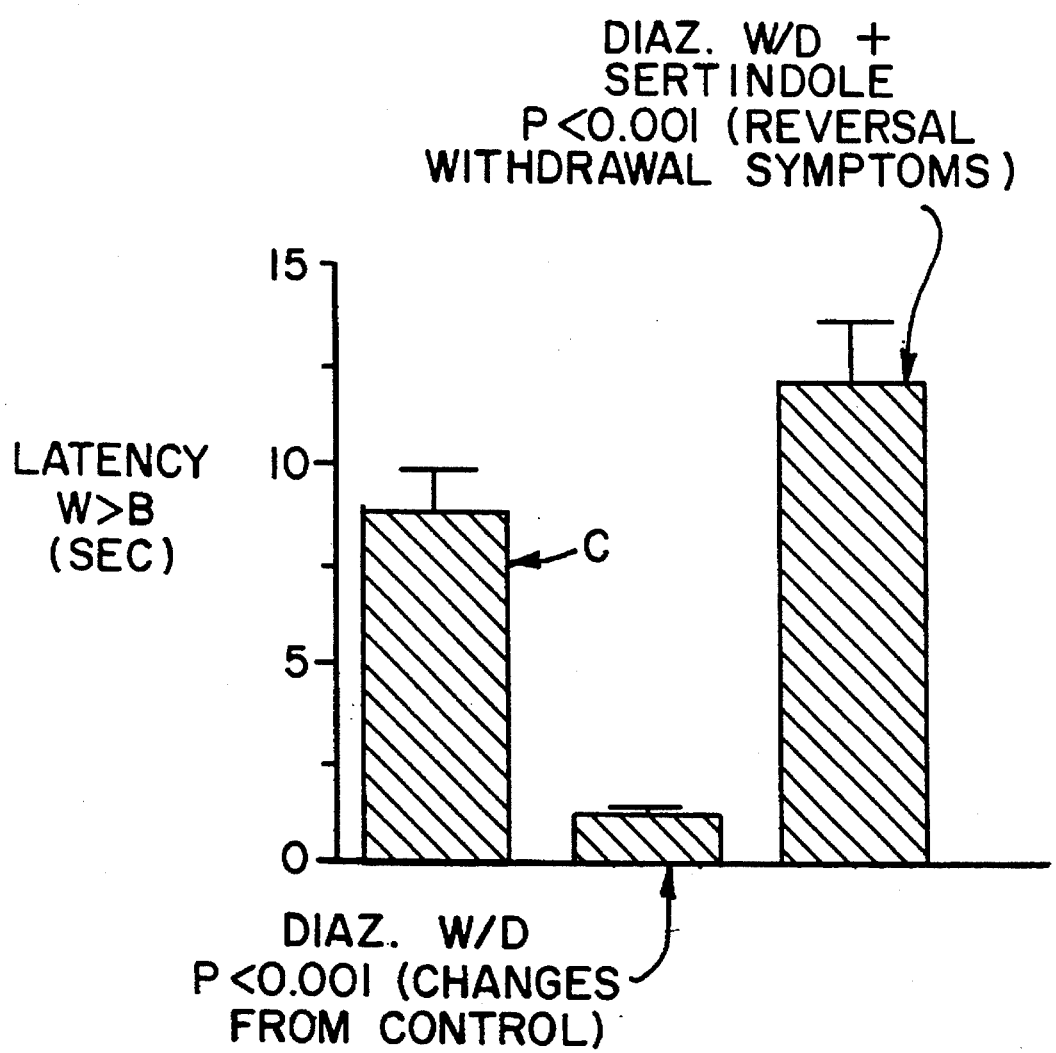

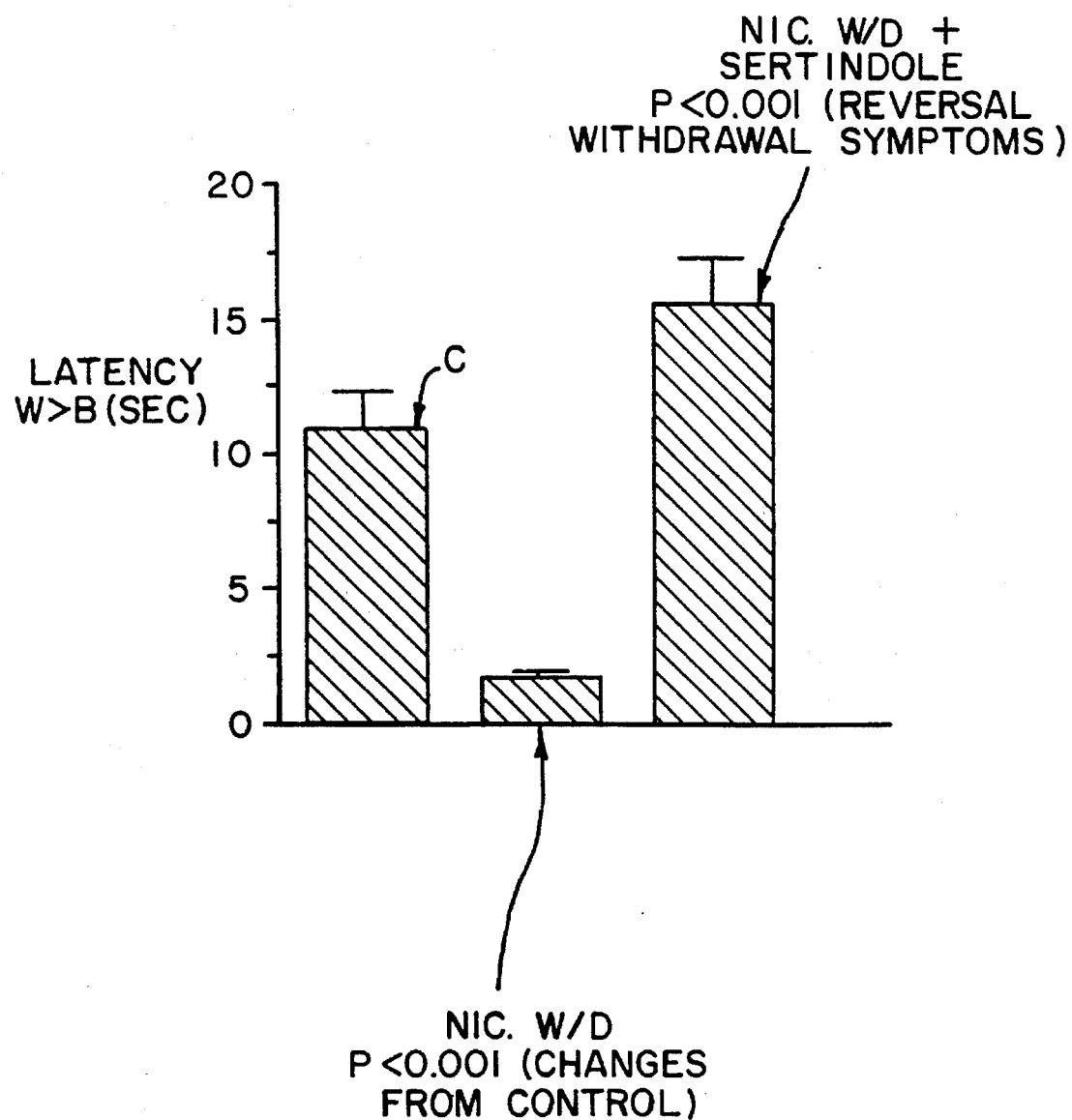

TREATMENT OF ADDICTION TO DRUGS AND SUBSTANCES OF ABUSE

This application is a national phase continuation of PCT/DK92/00062 filed Feb. 28, 1992 (WO 92/15302).

FIELD OF INVENTION

The present invention relates to the use of compounds belonging to a certain class of 1-aryl-3-(4-piperidyl)-indole derivatives for the treatment of addiction to drugs or substances of abuse such as alcohol or nicotine in man.

BACKGROUND OF THE INVENTION

U.S. Pat. No. 4,710,500 corresponding to EP 200,322B, discloses in general optionally 5-substituted 1-aryl-3-(4-piperidyl)—(I'), 1-aryl-3-(1-piperazinyl)—(II) or 1-aryl-3-(1,2,3,6-tetrahydro-4-pyridyl)-indole (III) derivatives having the formulas:

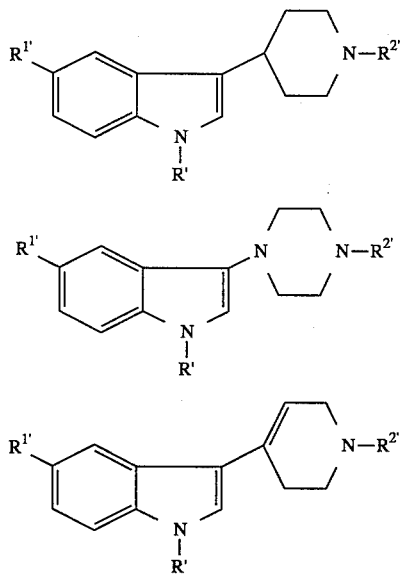

in which formulas R' designates optionally substituted phenyl or a hetero aromatic group, $R^{1'}$ is hydrogen or a substituent such as halogen, alkyl, alkoxy, cyano, nitro, etc, and $R^{2'}$ is hydrogen, alkyl, alkenyl or a certain heterocycle-lower alkyl substituent.

Most of the compounds are shown to be potent and long-lasting dopamine antagonists in vivo, and accordingly to be useful in the treatment of psychoses and all the compounds are proven to be strong serotonin-$S_2$ (5-hydroxytryptamine-2; 5-$HT_2$) receptor antagonists in vivo indicating effects in the treatment of depression and negative symptoms of schizophrenia. The tests used to show blockade of dopaminergic activity in vivo were a catalepsy test and a methylphenidate test, both being at that time regarded as tests for dopaminergic activity. However, at present said two tests are considered also to be a measure of the propensity of an antipsychotic compound to induce extrapyramidal side effects.

Though U.S. Pat. No. 4,710,500 generally comprises the 3-(4-piperidyl) compounds of the Formula I' disclosed above, only five such compounds have been specifically disclosed, i.e. 1-(4-fluorophenyl)-5-methyl-3-(1-methyl-4-piperidyl)-1H-indole, hydrobromide, designated Lu 21-037, 1-(4-fluorophenyl)-3-[1-[2-(2-imidazolidinon-1-yl)ethyl]-4-piperidyl]-1H-indole, designated Lu 23-086, 1-(4-fluorophenyl)-3-[1-[2-(2-pyrrolidinon-1-yl)ethyl]-4-piperidyl]-5-trifluoro-methyl-1H-indole, fumarate, designated Lu 23-158, 1-(4-fluorophenyl)-3-(1-methyl-4-piperidyl)-5-trifluoromethyl-1H-indole oxalate, designated Lu 21-131, 5-chloro-1-(4-fluorophenyl)-3-[1-[2-(2-imidazolidinon-1-yl)ethyl]-4-piperidyl]-1H-indole, sertindole.

The compound sertindole which is the compound of the above Formula I' wherin $R^{1'}$ is chloro, R' is 4-fluorophenyl and $R^{2'}$ is 2-(2-imidazolidinon-1-yl)ethyl is a known neuroleptic, the neuroleptic activity of which is described in the co-pending U.S. patent application Ser. No. 07/508,240 corresponding to EP 392,959A.

Our copending International Patent Application Publ. No. WO 92/00070 discloses the 3-(4-piperidyl) compounds of the formula I' as having anxiolytic activity without cataleptic activity and our copending International Patent Application No. PCT/ DK91/00291 describes prodrugs of sertindole.

Addiction with physical and psychological dependence to drugs such as cocaine, opiates, benzodiazepines, etc, and abuse of alcohol and nicotine and other substances causes great social and health problems all over the world. When the drug or substance of abuse is withdrawn from a dependant subject the subject develops physical and psychological withdrawal symptoms such as aggressive behaviour, agitation and intense craving for the drug or substance of abuse. Accordingly, withdrawal of such substances from addicts and abusers is very difficult, and no effective treatment of withdrawal symptoms and accordingly method of obtaining withdrawal is at present available. Accordingly, a compound which inhibits withdrawal symptoms or suppress dependence of drugs and other substances of abuse is highly desirable.

Surprisingly, it has now been found that certain 1-aryl-3-(4-piperidyl)-indole derivatives having the above general Formula I' in addition to the 5-$HT_2$ receptor antagonistic activity, also have alleviating, relieving or suppressing properties on withdrawal or abstinence symptoms and that they suppress the dependency of drug or substance of abuse. Furthermore they have been found to be non-cataleptic.

DISCLOSURE OF THE INVENTION

Accordingly the present invention provides the use of an 1-aryl-3-(4-piperidyl)-indole derivative having the general formula:

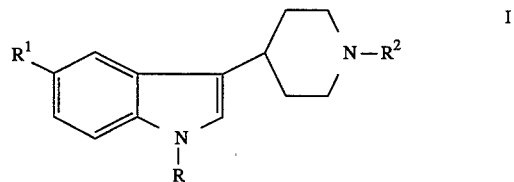

wherein $R^1$ is hydrogen, halogen, lower alkyl, lower alkoxy, hydroxy, cyano, nitro, lower alkylthio, trifluoromethyl, trifluoromethylthio, lower alkylsulfonyl, amino, lower alkylamino or lower dialkylamino;

R is phenyl optionally substituted with one or more substituents independently selected from the following: halogen, lower alkyl, lower alkoxy, hydroxy, trifluoromethyl, and cyano, or R is 2-thienyl, 3-thienyl, 2-furoyl, 3-furoyl, 2-thiazolyl, 2-oxazolyl, 2-imidazolyl, 2-pyridyl, 3-pyridyl, or 4-pyridyl; and $R^2$ is hydrogen, cycloalkyl, lower alkyl or lower alkenyl, optionally substituted with one or two hydroxy groups, any hydroxy group present being optionally esterified with an aliphatic carboxylic acid having from two to twentyfour carbon atoms inclusive, or $R^2$ is a group of the Formula IV:

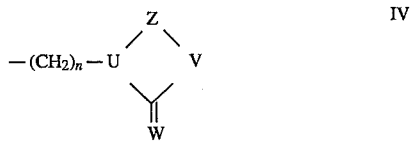

wherein n is an integer of from 2–6, inclusive;

W is O, S or N—$R^3$, wherein $R^3$ is H, lower alkyl or cycloalkyl U is N or CH;

Z is —$(CH_2)_m$—, m being 2 or 3, or Z is —CH=CH— or 1,2-phenylene optionally substituted with halogen or trifluoromethyl, or Z is —$COCH_2$— or —$CSCH_2$—;

V is O, S, $CH_2$, or $NR^4$, wherein $R^4$ is hydrogen, lower alkyl optionally substituted with one or two hydroxy groups, lower alkenyl or a cycloalkylmethyl group, said cycloalkyl having from three to six carbon atoms inclusive;

or a pharmaceutically acceptable acid addition salt thereof or prodrug therefore for the manufacture of a pharmaceutical preparation for alleviating, relieving or suppressing withdrawal or abstinence symptoms or suppressing the dependency of a drug or a substance of abuse.

In another aspect the present invention provides a method for alleviating, relieving or suppressing withdrawal or abstinence symptoms or suppressing the dependency of a drug or a substance of abuse comprising the step of administering a therapeutically effective amount of a compound having the Formula I as defined above to a person in need thereof.

The drugs causing the withdrawal symptoms may be opiates, such as morphine and heroine, cocaine, amphetamine, and benzodiazepines, such as diazepam, clonazepam, and nitrazepam, etc. In particular, the substances of abuse may be nicotine and alcohol.

The term "lower alkyl" is intended to mean a straight or branched alkyl group having from one to four carbon atoms, such as methyl, ethyl, n-propyl, iso-propyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

The term cycloalkyl designates a carbocyclic ring having 3–8 carbon atoms inclusive.

Lower alkenyl is intended to mean an alkenyl group containing from 2 to 4 carbon atoms, for example ethenyl, 1-propenyl, 2-butenyl, etc.

The Z-group —$COCH_2$— or —$CSCH_2$— may be oriented in either direction in the ring.

Some of the compounds of the general Formula I may exist in optical isomers thereof; and the administration of such optical isomers is also embraced by the method of the invention.

The Prodrugs used in the present invention may be conventional esters with available hydroxy groups, or in particular if the compound is a compound of the general Formula I wherein W is oxygen and V is >$NR^4$, $R^4$ being hydrogen, the prodrug may be formed by acylating the nitrogenatom of the V group and being accordingly represented by the Formula I wherein W is oxygen and V is >N—$R^{4'}$ wherein $R^{4'}$ designates a group —A—B, wherein A is selected from CO, CS, or $CH_2$, and if A is CO or CS, B is selected from the groups consisting of:

i) hydrogen, alkyl, alkenyl, cycloalkyl, cycloalkenyl or cycloalk(en)ylalk(en)yl, optionally substituted with one or two hydroxy groups, or phenyl optionally substituted with one or more substituents selected from the group consisting of halogen, trifluoromethyl, lower alkyl, lower alkoxy, lower alkylthio, acyloxy, or cyano; or ii) $QR^5$, wherein Q is O or S and $R^5$ is selected from the substituents defined for B under i) above; and iii) $NR^6R^7$, wherein $R^6$ and $R^7$ independently are selected from the substituents defined for B under i) above, or $R^6$ and $R^7$ are combined to form a four to eight membered heterocyclic ring containing from one to three nitrogen atoms and from zero to three oxygen or sulfur atoms; or if A is $CH_2$, B is selected from the groups consisting of:

iv) a group $QR^5$ as defined in ii);

v) a group $NR^6R^7$ as defined in iii); or vi) a group $OC(O)R^8$, wherein $R^8$ is as defined for B under i).

Although the latter prodrugs are not esters, they have been found to decompose properly in order to release the compound of the invention over an desired period of time when administered parenterally as a depote formulation in an appropriate oil, such as coconut oil, e.g. viscoleo®, peanut oil, sesame oil, cotton seed oil, corn oil, soy bean oil, olive oil, etc. or synthetic esters of fatty acids and glycerol or propyleneglycol.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

The compounds of the Formula I and the pharmaceutically acceptable acid addition salts thereof may be administered in any suitable way, e.g. orally or parenterally, and the compounds may be presented in any suitable form for such administration, e.g. in the form of tablets, capsules, powders, syrups or solutions or dispersions for injection.

An effective daily dose of a compound of the Formula I or a pharmaceutically acceptable salt thereof may be from 1.0 μg/Kg to 1.0 mg/Kg body weight.

The compounds used in the method of the invention have been found to show effects in in vivo drug, and substance of abuse withdrawal tests in mice, and they have been found not to induce catalepsy or only induce weak catalepsy (cf. Our Internat. Patent Application Publ. No. WO 92/00070) which is today regarded as indicative of extrapyramidal side effects. It is indeed very surprising that the present compounds are non-cataleptic whereas the compounds of the Formulas II and III of the above U.S. patent have proved to be cataleptic (c.f. the pharmacological data in the following) and the mechanisms behind this are not fully understood. Accordingly the compounds of the present invention are believed to be useful in treatment of addiction to drugs and substances of abuse, particularly in the relieving or alleviating the withdrawal symptoms and reducing the dependency, without causing the extrapyramidal side effects known from traditional psychotropics.

Certain imidazolyl-pyridoindol and Imidazolyl-azepinoindol compounds known to be selective 5-$HT_3$ receptor antagonists and alleged to have anxiolytic effects have been disclosed also to have effects on withdrawal of drugs and other substances of abuse, EP Patent Publication No. 357 415 A2. However, the compounds used in the present invention which have also been found to be anxiolytic (c.f our copending International Patent Application No. WO 92/00070) are very different chemical structures without effects on the 5-$HT_3$ receptor in the brain. Furthermore it is known that other anxiolytics, such as the benzodiazepines, do not show effects in the above mentioned tests. Additionally the known anxiolytic buspirone do not counteract abstinence syndrome (Schweizer and Rickels, Am. J. Psychiat., 143: 1590:1592 (1986)). Accordingly, the mechanisms of action on withdrawal symptoms are either different from those of the compounds of EP Patent Publication No. 357 415 A2 or they are due to common activities not known.

BRIEF DESCRIPTION OF THE DRAWINGS

FIGS. 1a–1d illustrate the effect of administration of a compound of the invention, i.e. sertindole in a dose of 0.1 mg/kg i.p., on withdrawal symptoms following diazepam treatment.

FIGS. 2a–2d illustrate the effect of administration of a compound of the invention, i.e. sertindole in a dose of 0.1 mg/kg i.p., on nicotine withdrawal symptoms.

DETAILED DESCRIPTION OF THE INVENTION

Figure 2A:
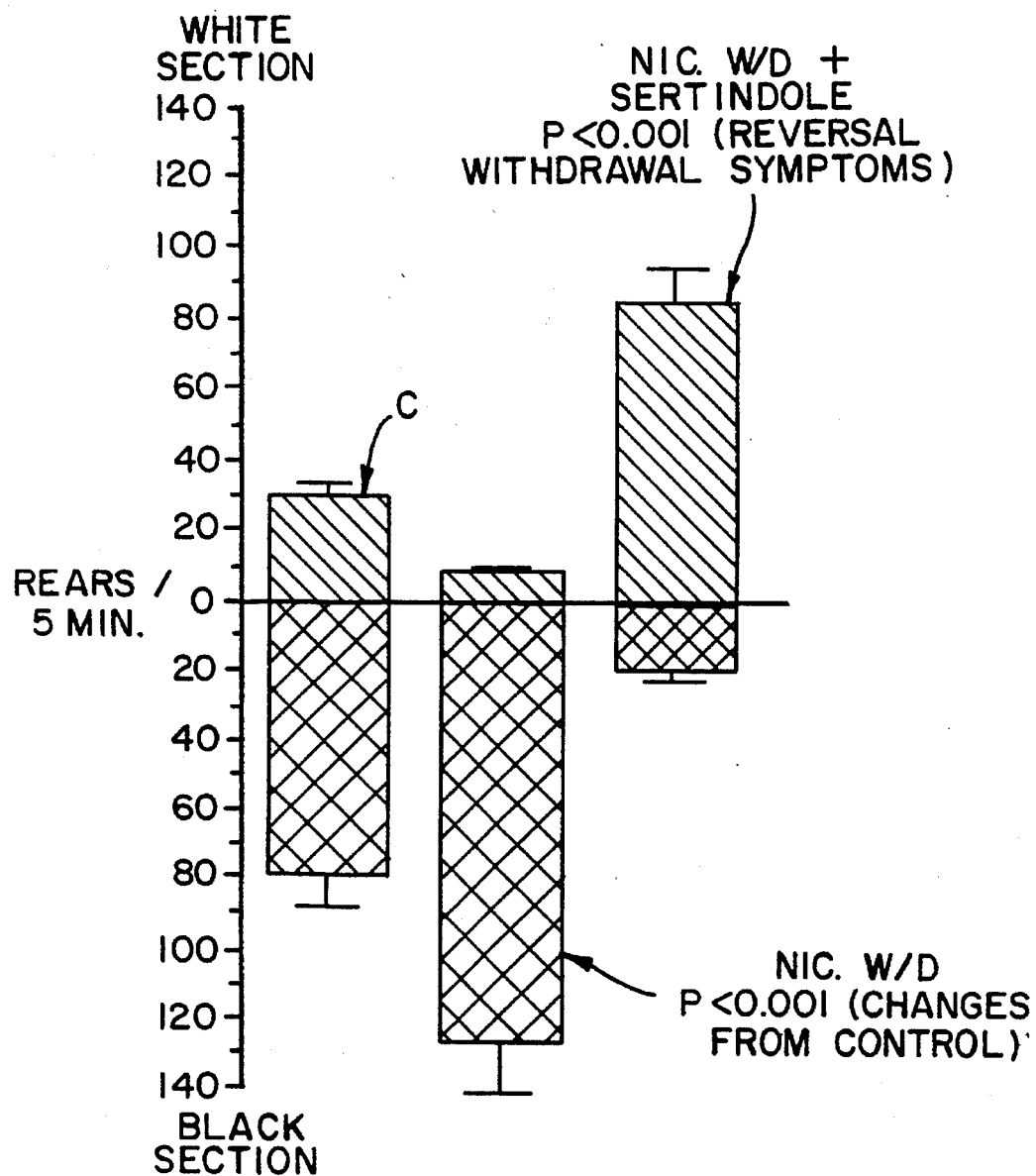

In a preferred embodiment of the invention the compound used is a compound of the Formula I as defined in the foregoing wherein R is phenyl substituted in 4 position with fluoro, or R is 2- or 3-thienyl;

$R^1$ is hydrogen, halogen, lower alkyl, lower alkoxy, cyano, trifluoromethyl, or lower alkylsulphonyl;

$R^2$ is a group having the Formula IV as defined in the foregoing wherein n=2–6;

W is O or S;

U is N;

Z is —$(CH_2)_2$—, —$(CH_2)_3$—, or —CH=CH—; and v is O, $CH_2$ or $NR^4$, $R^4$ being hydrogen or lower alkyl;

or a pharmaceutically acceptable acid addition salt thereof or prodrug therefor.

A particularly preferred compound used in the invention is the compound of formula wherein $R^1$ is chloro, R is 4-fluorophenyl and $R^2$ is 2-(2-imidazolidinon-1-yl)ethyl known as sertindole.

The compounds of the Formula I used in the invention may be prepared according to methods (b), (c), or (d) described in U.S. Pat. No. 4,710,500. 2-pyrrolidinthiones are prepared from the corresponding lactame derivatives according to literature methods (Bull.Soc.Chim.Belg. 87, 223, 229, 299, 525 (1978)) by using Lawesson's reagent or phosphorous pentasulphide at appropriate temperatures. Imidazolidin-2-thion derivatives are prepared by ringclosure reactions from properly substituted ethylenediamines with carbondisulphide, thiophosgen or corresponding thiocarbonyl precursor compounds.

5-Hydroxy substituted indoles are prepared by conventional methods of demethylation of the coresponding methyl ethers. Pyridine hydrochloride or hydrobromide or methionin in methanesulphonic acid is used to split off the methyl group.

The 5-cyano compounds are prepared by substitution of 5-bromo or 5-iodo in the appropriate substituted compounds using CuCN in an aprotic polar solvent such as N,N-dimethylformamide, N-methyl-2-pyrrolidone (NMP) or HMPA at elevated temperatures.

The acid addition salts of the compounds used in the invention are easily prepared by methods well known in the art. The base is reacted with either the calculated amount of organic or inorganic acid in an aqueous miscible solvent, such as acetone or ethanol, with isolation of the salt by concentration and cooling, or an excess of the acid in an aqueous immiscible solvent such as ethyl ether or chloroform with the desired salt separating directly. Of course, these salts may also be prepared by the classical method of double decomposition of appropriate salts.

In addition to the substances specifically mentioned in U.S. Pat. No. 4,710,500, specific examples of compounds used according to the invention are the following compounds which were prepared according to methods (b), (c), or (d) described in U.S. Pat. No. 4,710,500 or from the corresponding lactame derivatives according to litterature methods (Bull.Soc.Chim.Belg. 87, 223, 229, 299, 525 (1978)) by using Lawesson's reagent or phosphorous pentasulphide at appropriate temperatures:

5-chloro-1-(4-fluorophenyl)-3-[1-(2-hydroxyethyl)-4-piperidyl]-1H-indole, hydrochloride, 1 MP: 266°–269° C.

5-chloro-1-(4-fluorophenyl)-3-[1-[2-(2-oxazolidinon-1-yl)ethyl]- 4-piperidyl]-1H-indole, fumarate, 2, MP: 203°–205° C.

5-chloro-1-(4-fluorophenyl)-3-[1-[2-(3-methyl-2-imidazolidinon- 1-yl)ethyl]-4-piperidyl]- 1H-indole, fumarate, 3, MP: 198°–199° C.

5-chloro-1-(4-fluorophenyl)-3-[1-[2-(2-pyrrolidinon-1-yl)ethyl]- 4-piperidyl]-1H-indole, fumarate, 4, MP: 209°–211° C.

1-(4-fluorophenyl)-3-[1-[2-(3-methyl-2-imidazolidinon-1-yl)ethyl]- 4-piperidyl]-5-trifluoromethyl- 1H-indole, 5, MP: 144°–145° C.

1-(4-fluorophenyl)-3-[1-[2-(2-oxazolidinon-1-yl)ethyl]-4-piperidyl]- 5-trifluoromethyl-1H-indole, fumarate, 6, MP: 212°–213° C.

5-chloro-1-(4-fluorophenyl)-3-[1-[2-(2-pyrrolidinthion-1-yl)ethyl]- 4-piperidyl]-1H-indole, fumarate, 7, MP: 195°–199° C.

1-(4-fluorophenyl)-3-[1-[2-(2-imidazolidinon-1-yl)ethyl] -4-piperidyl]- 5-methylsulfonyl- 1H-indole, fumarate, 8, MP: 188°–192° C.

5-chloro-1-(4-fluorophenyl)-3-[1-[6-(2-pyrrolidinon-1-yl)-1-hexyl]- 4-piperidyl]-1H-indole,hydrochloride, 9, MP: 123°–128° C.

5-chloro-1-(4-fluorophenyl)-3-(4-piperidyl)-1H-indole, fumarate, 10, MP: 192°–201 ° C.

1-(4-fluorophenyl)-3-(4-piperidyl)-5-trifluoromethyl-1H- indole, hydrochloride, 11 MP: 281°–284° C.

1-(4-fluorophenyl)-3-[1-[2-(2-imidazolidinon-1-yl)ethyl]-4-piperidyl]- 5-trifluoromethyl- 1H-indole, 12, MP: 169°–171° C.

1-(4-fluorophenyl)-3-[1-[6-(2-pyrrolidinon-1-yl)-1-hexyl]-4-piperidyl]- 5-trifluoromethyl- 1H-indole,oxalate, 13, MP: 85°–87° C.

5-chloro-1-(4-fluorophenyl)-3-[1-[2-[3-(2-propyl)-2-imidazolidinon- 1-yl]ethyl]-4-piperidyl]-1H-indole, oxalate, 14, MP: 92°–96° C.

5-fluoro-1-(4-fluorophenyl)-3-(4-piperidyl)-1H-indole, fumarate, 15, MP: 198°–200 ° C.

5-fluoro-1-(4-fluorophenyl)-3-[1-[2-(2-imidazolidinon-1-yl)ethyl]- 4-piperidyl]-1H-indole, oxalate, 16, MP: 188°–190° C.

5-fluoro-1-(4-fluorophenyl)-3-[1-[2-(2-pyrrolidinon-1-yl)ethyl]- 4-piperidyl]-1H-indole, fumarate, 17, MP: 178°–180° C.

5-fluoro-1-(4-fluorophenyl)-3-[1-[2-[3-(2-propyl)-2-imidazolidinon- 1-yl]ethyl]-4-piperidyl]- 1H-indole, fumarate, 18, MP: 115°–120° C.

5-chloro-1-(4-fluorophenyl)-3-[1-[5-(2-imidazolidinon-1-yl)-1-pentyl]- 4-piperidyl]-1H-indole, oxalate, 19, MP: 145°–147° C.

5-chloro-1-(4-fluorophenyl)-3-[1-[4-(2-imidazolidinon-1-yl)-1-butyl]- 4-piperidyl]-1H-indole, oxalate, 20, MP: 178°–179° C.

5-chloro-1-(4-fluorophenyl)-3-[1-[6-(2-imidazolidinon-1-yl)-1-hexyl]- 4-piperidyl]-1H-indole, oxalate, 21, MP: 156°–158° C.

5-chloro-1-(4-fluorophenyl)-3-[1-[2-(hydantoin-2-yl)ethyl]-4-piperidyl]- 1H-indole, 22, MP: 174°–176° C.

5-fluoro-1-(4-fluorophenyl)-3-[1-[6-(2-pyrrolidinon-1-yl)-1-hexyl]- 4-piperidyl]-1H-indole, 23, oil 1-(4-fluorophenyl)-3-[1-[2-(2-imidazolidinon-1-yl)ethyl]-4-piperidyl]- 5-methyl-1H-indole, 24, MP: 187°–189° C.

1-(4-fluorophenyl)-3-[1-[2-[3-(2-propyl)-2-imidazolidinon-1-yl]ethyl]- 4-piperidyl]-5-methyl- 1H-indole, hydrochloride, hydrate, 25, MP: 214°–215° C.

1-(4-fluorophenyl)-3-[1-[2-(2-pyrrolidinon-1-yl)ethyl]-4-piperidyl]- 5-methyl-1H-indole, hydrochloride, hemihydrate, 26, 265°–266° C.

1-(4-fluorophenyl)-3-[1-[2-[3-(2-propyl)-2-imidazolidinon-1-yl]ethyl]- 4-piperidyl]-5-trifluoromethyl- 1H-indole, 27, MP: 99°–100° C.

3-[1-[2-(2-imidazolidinon-1-yl)ethyl]-4-piperidyl]-1-(3-thienyl)-1H-indole, oxalate 28, MP: 139°–140° C.

1-(4-fluorophenyl)-3-[1-[2-(2-imidazolidinon-1-yl)ethyl]-4-piperidyl]- 5-methoxy-1H-indole, 29, MP: 167° C.

5-fluoro-3-[1-[2-[3-(2-propyl)-2-imidazolidinon-1-yl]ethyl]- 4-piperidyl]-1-(3-thienyl)-1H-indole, oxalate, hemihydrate, 30, MP: 95°–97° C.

5-fluoro-3-[1-[2-[3-(2-propyl)-2-imidazolidinon-1-yl]ethyl]- 4-piperidyl]-1-(2-thienyl)-1H-indole, dioxalate, 31, MP: 173°–174° C.

5-bromo-1-(4-fluorophenyl)-3-[1-[2-(2-imidazolidinon-1-yl)ethyl]- 4-piperidyl]-1H-indole, 32, MP: 171°–172° C.

1-(4-fluorophenyl)-3-[1-[2-[3-(2-propyl)-2-imidazolidinon-1-yl]ethyl]- 4-piperidyl]-1H-indole, hydrochloride, 33, MP: 226°–227° C.

5-chloro-1-(4-fluorophenyl)-3-[1-[3-(2-imidazolidinon-1-yl)-1-propyl]- 4-piperidyl]-1H-indole, fumarate, 34, MP: 203°–205° C.

In the following examples the preparation of an imidazolidin-2-thion derivative and of two derivatives having a hydroxyl and a cyano group, respectively, in the 5-position of the indole ring is shown:

EXAMPLE 1

5-chloro-1-(4-fluorophenyl)-3-[1-[2-(2-imidazolidinthion-1-yl)ethyl]- 4-piperidyl]-1H-indole, oxalate, 35, MP: 150° C.

To a solution of 5-chloro-1-(4-fluorophenyl)-3-(4-piperidyl)-1H-indole (25 g) in N-methyl- 2-pyrrolidone (150 ml) were added chloroacetonitrile (6 g) and triethylamine (10 ml). The reaction mixture was heated at 60° C. for one hour and subsequently poured onto crushed ice. The precipitated 5-chloro-3-(1-cyanomethyl-4-piperidyl-1-(4-fluorophenyl)- 1H-indole was filtered off and washed with warm water. Yield 20 g. MP: 170°–172° C.

A solution of the thus isolated cyanomethylderivative (24 g) in dry THF (150 ml) was added dropwise to a previously prepared solution of AlH$_3$ (from 8 g of LiAlH$_4$ and 8 g of AlCl$_3$) in dry diethyl ether (250 ml). The mixture was heated at reflux for one hour and finally hydrolyzed by carefully adding a conc. aqueous solution of NaOH (10 ml) under simultaneous cooling. Inorganic salts were filtered off and were subsequently carefully washed with hot dichloromethane (2×100 ml). the combined organic phases were dried (anh. MgSO$_4$) and finally evaporated leaving 3-[1-(2-aminoethyl)-4-piperidyl]- 5-chloro-1-(4-fluorophenyl)-1H-indole (25 g) as an oil. Without further purification this product (12 g) and triethylamine (4.2 g) were heated in 1,1,1-trichloroethane (100 ml) at 50°–55° C. A solution of chloroacetonitrile (3.6 g) in 1,1,1-trichloroethane (10 ml) were added dropwise during 10 minutes. The mixture was heated for another 4 hours at 50° C. Ethyl acetate (200 ml) was added and the mixture was poured into ice cooled dil. aqueous NaOH solution (400 ml). The organic phase was separated, washed with brine, dried (anh. MgSO$_4$) and the solvents evaporated leaving 5-chloro-3-[1-[2-(N-cyanomethyl)aminoethyl]-4-piperidyl]-1-( 4-fluorophenyl)-1H-indole (14 g) as an oil.

The oil thus isolated was dissolved in dry THF (100 ml) and added dropwise to a previously prepared solution of AlH$_3$ (from 6 g of LiAlH$_4$ and 6 g of AlCl$_3$) in dry diethyl ether (200 ml). The mixture was refluxed for one hour and finally hydrolyzed by cautiously adding a conc. aqueous solution of NaOH (8 ml) under simultaneous cooling. Inorganic salts were filtered off and were subsequently washed with hot dichloromethane (2×100 ml). The combined organic phases were dried (anh. MgSO$_4$) and finally evaporated leaving 3-[1-[N-(2-aminoethyl)-2-aminoethyl]-4-piperidyl]- 5-chloro-1-(4-fluorophenyl)-1H-indole (8.5 g) as an oil. This oil (4.5 g) was dissolved in 1-pentanol (50 ml) and carbondisulphide (5 ml) was added. After stirring for 2 hours at room temperature the resulting suspension was heated to 140° C. for 1.5 hours. Excess CS$_2$ was flushed away by a gentle stream of N$_2$ gas. Finally most of the 1-pentanol was evaporated at reduced pressure. The remaining oil was purified by column chromatography on silica gel (eluted with ethyl acetate/ethanol/triethylamine— 80/20/4). The oxalate salt of the title compound 35 crystallized from acetone. Yield 250 mg. MP: 150° C.

EXAMPLE 2

1-(4-Fluorophenyl)-5-hydroxy-3-[1-[2-(2-imidazolidinon-1-yl)ethyl]-4-piperidyl]-1H-indole. 36, MP: 220° C.

Pyridinhydrochloride (60 g) and 1-(4-fluorophenyl)-3-[1-[2-(2-imidazolidinon- 1-yl)ethyl]- 4-piperidyl]-5-methoxy-1H-indole, compound 29 (6 g) were mixed and heated to 180° C. under $N_2$ for 1½ hours. After cooling, water (300 ml) and ethyl acetate (100 ml) were added. By addition of $NH_4OH$ solution the pH was adjusted to >9. The organic phase was separated, washed with water (50 ml), dried (anh. $MgSO_4$), and the solvent evaporated leaving the phenolic crude title compound as an oil. Purification by column chromatography on silica gel (eluted with ethyl acetate/dichloromethane/ethanol/triethylamine 60:20:20:5) afforded the title compound 36 as a crystalline material. Yield: 1.9 g. MP: 220° C.

EXAMPLE 3

5-Cyano-1-(4-fluorophenyl)-3-[1-[2-(2-imidazolidinon-1-yl)ethyl]-4-piperidyl]-1H-indole, 37, MP: 209° C.

To a solution of 5-bromo-1-(4-fluorophenyl)-3-(4-piperidyl)-1H-indole (17 g) in dichloromethane (170 ml) was added a solution of ditert.-butyloxycarbonate (12 g) in dichloromethane (30 ml). After stirring for 30 minutes at room temperature the dichloromethane was evaporated in vacuo. 5-Bromo-3-(1-tert-butyloxycarbonyl-4-piperidyl)-1-(4-fluorophenyl)-1H-indole crystallized from n-heptane. Yield: 14 g. MP: 155° C. All the crystalline material was dissolved in N-methyl-2-pyrrolidone (75 ml) and CaCN (5 g) was added. The mixture was heated at 160° C. for 6 hours. The mixture was then poured into a solution of NaCN (10 g) in water (200 ml) and stirred for 20 minutes. Diethyl ether (200 ml) was added. The ether phase was separated, washed with brine (50 ml), dried (anh. $MgSO_4$), and the ether evaporated leaving a mixture of 5-bromo and 5-cyano compounds which were separated by coloumn chromatography on silica gel (eluted with diethyl ether). The 3-(1-tert.butyloxycarbonyl- 4-piperidyl)-5-cyano-1-(4-fluorophenyl)-1H-indole was isolated an an oil. Yield: 4.5 g. The protecting group—tert.butyloxycarbonyl—was splitted off by standard acidic ($CF_3COOH$) decomposition. The thus obtained 5-cyano-1-(4-fluorophenyl)- 3-(4-piperidyl)-1H-indole (3.2 g) was dissolved in methyl isobutyl ketone (90 ml). Potassium carbonate (4.5 g), potassium iodide (0.5 g) and 1-(2-chloroethyl)- 2-imidazolidinone (2.3 g) were added. The mixture was refluxed for 16 hours. After cooling inorganic salts were filtered off, and the organic solvent evaporated. Water (100 ml) and ethyl acetate (50 ml) were added. The organic phase was separated, dried (anh. $MgSO_4$), and finally ethyl acetate evaporated leaving the crude title compound as an oil. Purification by column chromatography on silica gel (eluted with ethyl acetate/ethanol/triethylamine 80:20:4) afforded 2.1 g of pure crystalline title compound, 37. MP: 209° C.

PHARMACOLOGY

The compounds used in the invention were tested in accordance with well recognized and reliable test methods. The tests were as follows:

CATALEPSY TEST

Evaluation of catalepsy is made according to Arnt (Eur. J. Pharmacol. 90, 47–55 (1983)). Test compound is given s.c. in different doses. The rat (170–240 g) is placed on a vertical wire mesh (mesh diameter 12 mm). The rat is considered cataleptic if it remains immobile for more than 15 sec. The maximum number of rats showing catalepsy within the first 6 hours is recorded for each dose group. The results are recorded in fractions and an $ED_{50}$ value is calculated by means of log-probit analysis. The results are shown in Table 1 (cf. Our Internat. Patent Application Publ. No. WO 92/00070).

The following corresponding 1-aryl-3-(1,2,3,6-tetrahydrpyridyl)- or 1-aryl-3-(piperazinyl)indole derivatives which are analogues of sertindole and compound No. 12, respectively, were included in the test as comparing compounds:

1-(4-Fluorophenyl)-3-[1-[2-(2-imidazolidinon-1-yl)ethyl]- 1,2,3,6-tetrahydropyridin-4-yl]- 5-trifluoromethyl-1H-indole (Comp. A)

5-Chloro-1-(4-fluorophenyl)-3-[1-[2-(2-imidazolidinon-1-yl)ethyl]- 1,2,3,6-tetrahydro-4-pyridyl]- 1H-indole (Comp. B)

5-Chloro-1-(4-fluorophenyl)-3-[4-[2-(2-imidazolidinon-1-yl)ethyl]- 1-piperazinyl]-1H-indole (Comp C)

TABLE 1

| Compound | Cataleptic Activity ED50(s.c.) (µmol/kg) |
| --- | --- |
| Sertindole | >98 |
| Comp. No 12 | 38 |
| Comp. No 2 | >18 |
| Comp. No 3 | 31 |
| Comp. No 4 | 23 |
| Comp. No 14 | >69 |
| Comp. No 16 | >78 |
| Comp. No 24 | >95 |
| Comp. A | 0.49 |
| Comp. B | 2.2 |
| Comp. C | 4.5 |

Further $ED_{50}$ values of corresponding 1-aryl-3-(1,2,3,6-tetrahydro-4-pyridyl)- or 1-aryl- 3-(1-piperazinyl)indole derivatives are given in U.S. Pat. No. 4,710,500.

INHIBITION OF WITHDRAWAL SYMPTOMS IN MICE

The tests are tests for the effect of a substance on the abstinence symptoms induced by withdrawal of a drug of a substance of abuse in mice measured as the effect on some specific behavioral changes following to withdrawal of the drug or substance of abuse. Such an animal model has been shown to be indicative of effects on withdrawal symptoms (Barry et al. Pharmac. Biochem. Behav. 27:239– 245 and Costall et al. Pharmac. Biochem. Behav., 33, 1989, 197, and Kelly et al. Eur. Neurosci. Ass. Winter Scool Meet. Zuos, Switzerland, 10–17th Jan. 1987).

Materials

The test was conducted using an open-top experimental box (45*27*27 cm) two fifths of which was partitioned from the rest, painted black and illuminated with a dim red light (1×60 W, zero Lux). The remainder of the box was painted white and brightly illuminated (60 W, 400 Lux) with a white light source. The light sources were located 17 cm above the box and the base of the box was lined into 9 cm squares. Access between the two compartments was by means of a 7.5×7.5 cm opening located in floor level at the centre of the partition.

The mice were male BKW mice having weight of 25–30 g, housed in groups of 10 and given free acces to drink and food and kept on a dark/light cycle of 12 hours.

A) Diazepam Withdrawal

Diazepam (10 mg/kg) was given i.p. twice a day for 7 days and then withdrawn. At the time of the last dose the mice received test substance, and on the following day they received a dose of test substance at 8 a.m. and another 40 min. prior to testing.

The test was carried out by taking the mice to a dimly illuminated room and then after 1 hour adaption to the new environment placing them in the centre of the white section of the test box. Behavioural changes were assed via remote video recording. The following behavioural changes were measured:

a) The time spent in the white and black section;

b) the number of explorative rearings in both the white and black section;

c) the number of line crossings in the white and black section; and d) the latency of the initial movement from the white to the black area.

Separate groups of mice were used for each behavioural assessment and the experiment was carried out blind. The control group represent the mean control data for 15 mice.

The results are shown graphically in FIG. 1 for one compound according to the invention, i.e. sertindole, administered in a dose of 0.1 mg/kg.

B) Nicotine Withdrawal

The experimental design was as described for the diazepam withdrawal studies. Nicotine was given (0.1 mg/kg i.p., b.d) for 7 days and test compound was given with the last dose of nicotine. Animals were tested on the following day after receiving a total of 3 doses of test compound. The assesment of the behavioural changes was as described for diazepam.

Figure 2B:
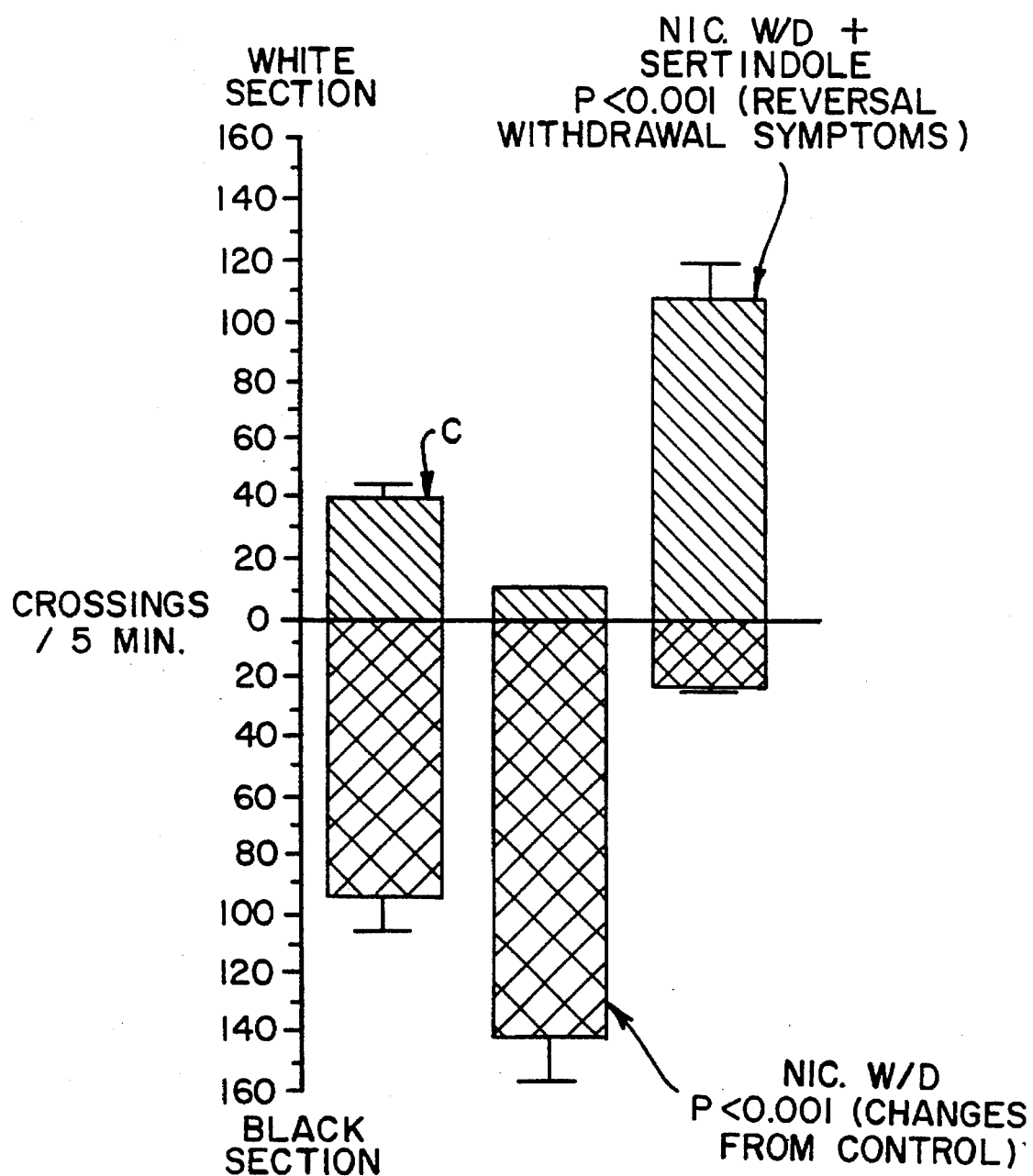
Figure 2C:
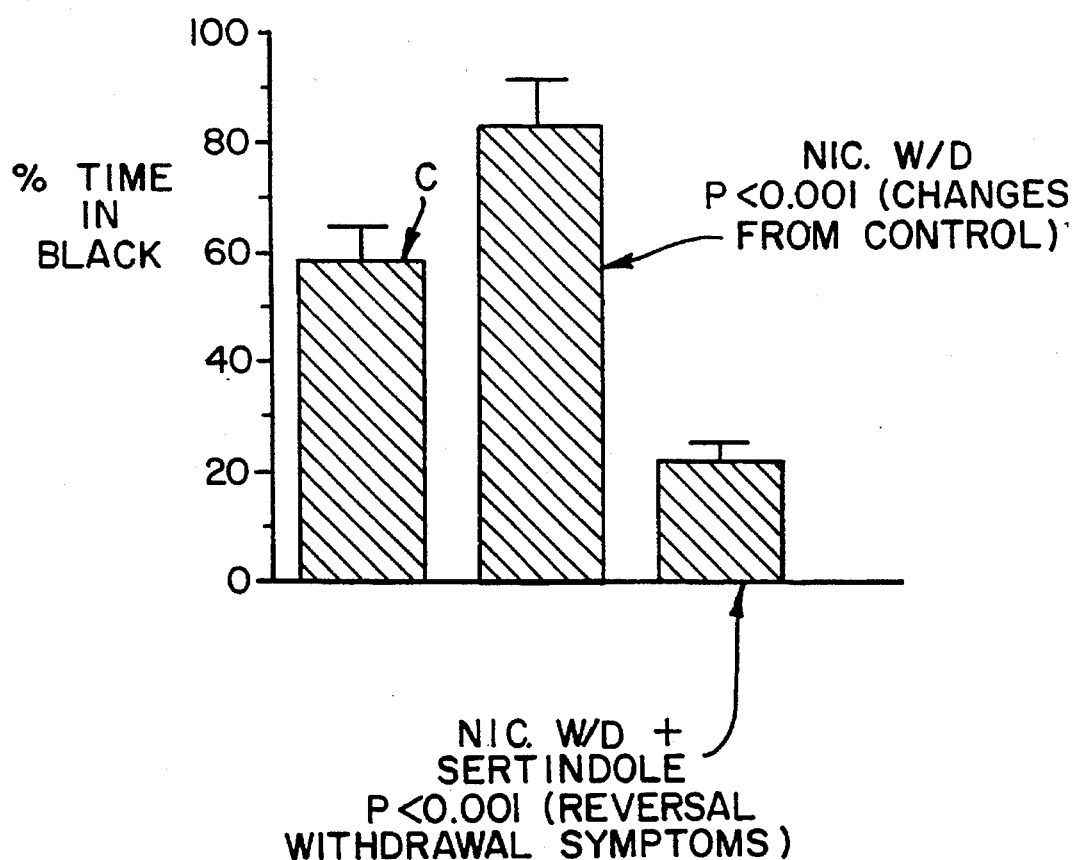
Figure 3A:
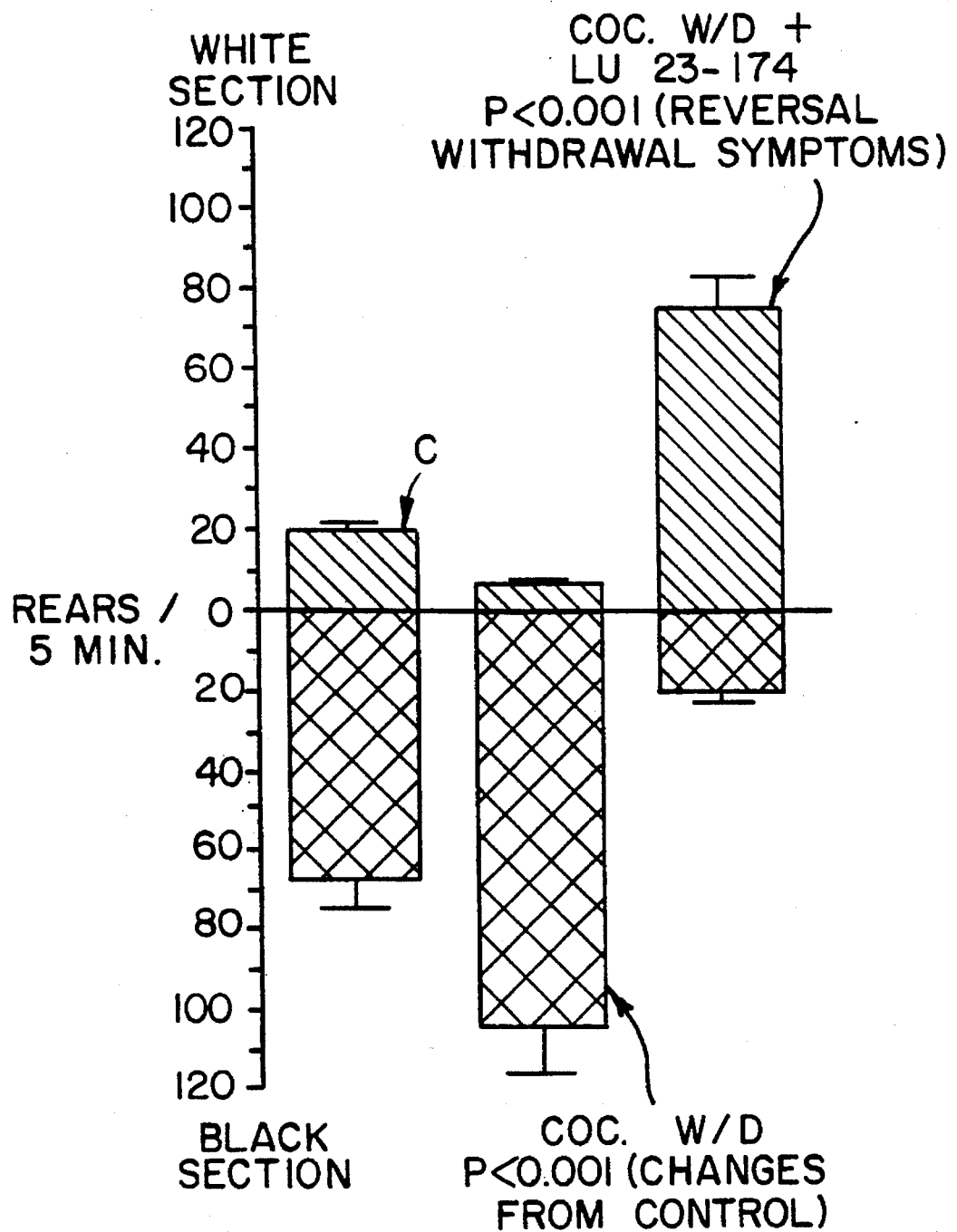
FIGS. 3a–3d illustrate the effect of administration of a compound of the invention, i.e. sertindole in a dose of 0.1 mg/kg i.p., on cocaine withdrawal symptoms.
Figure 3B:
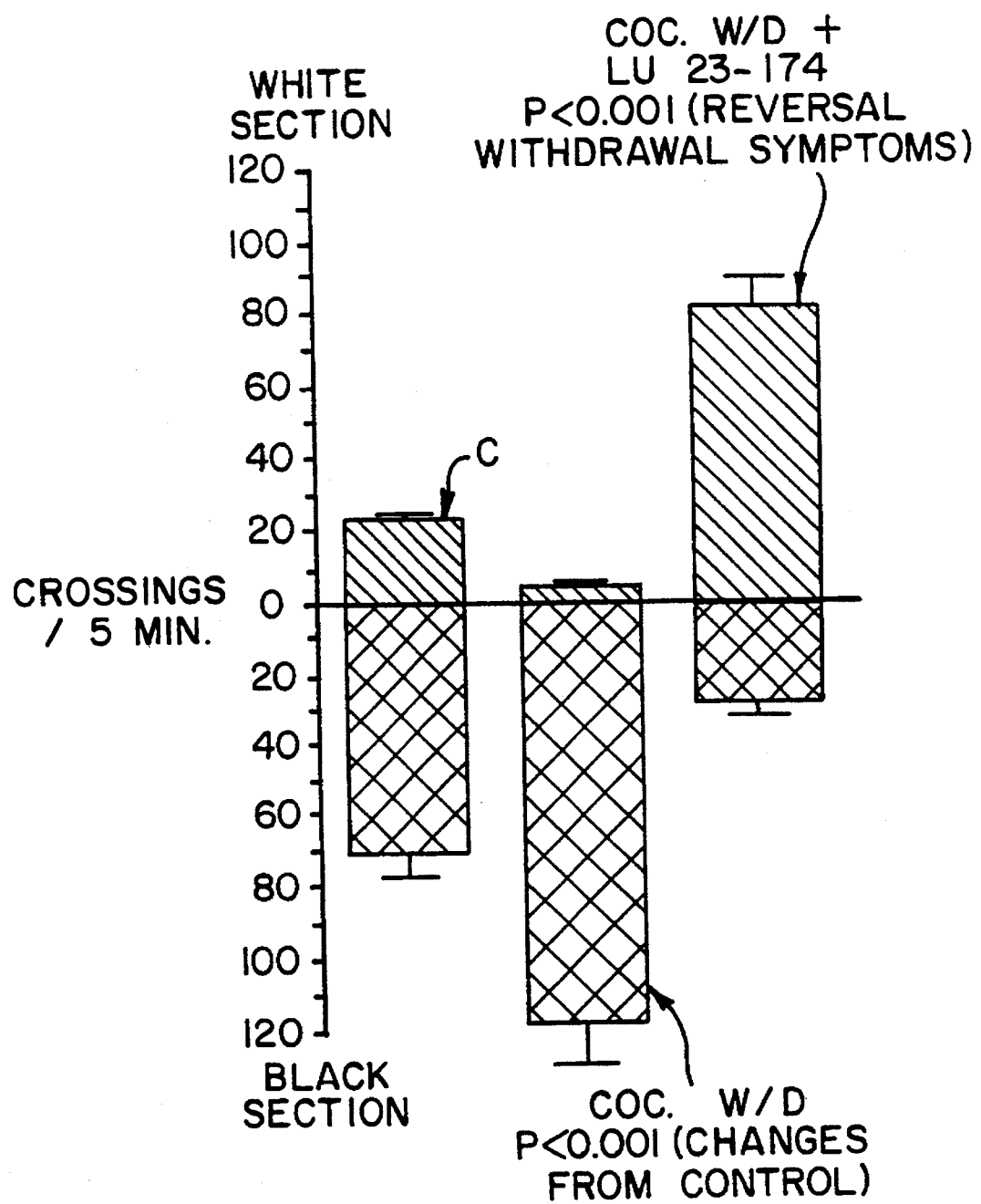
Figure 3C:
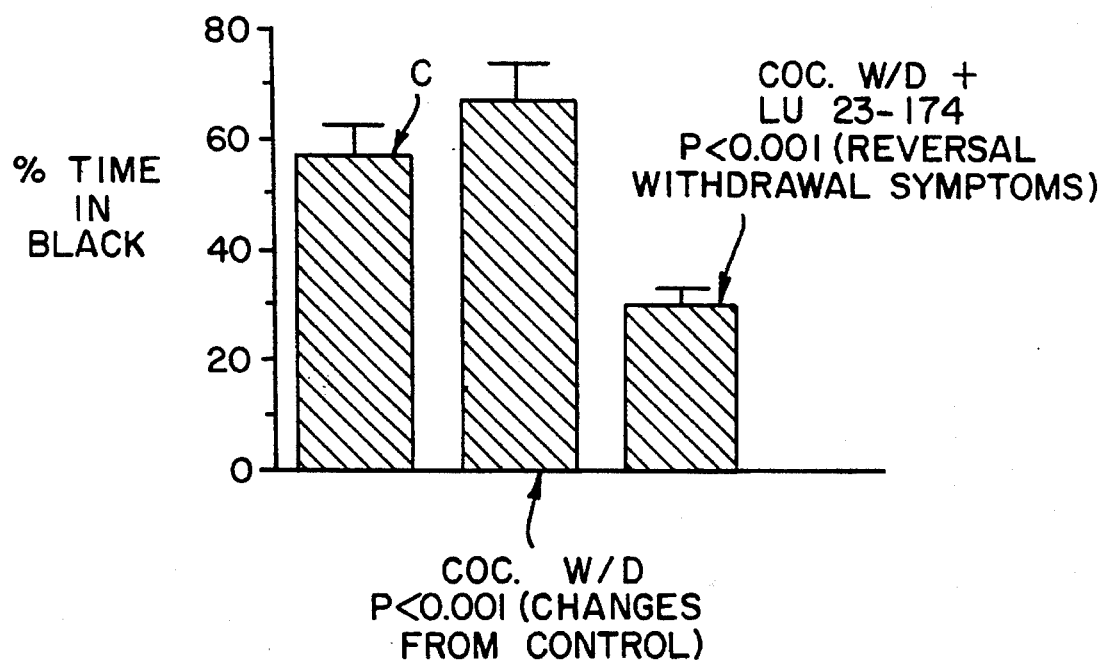
Figure 3D:
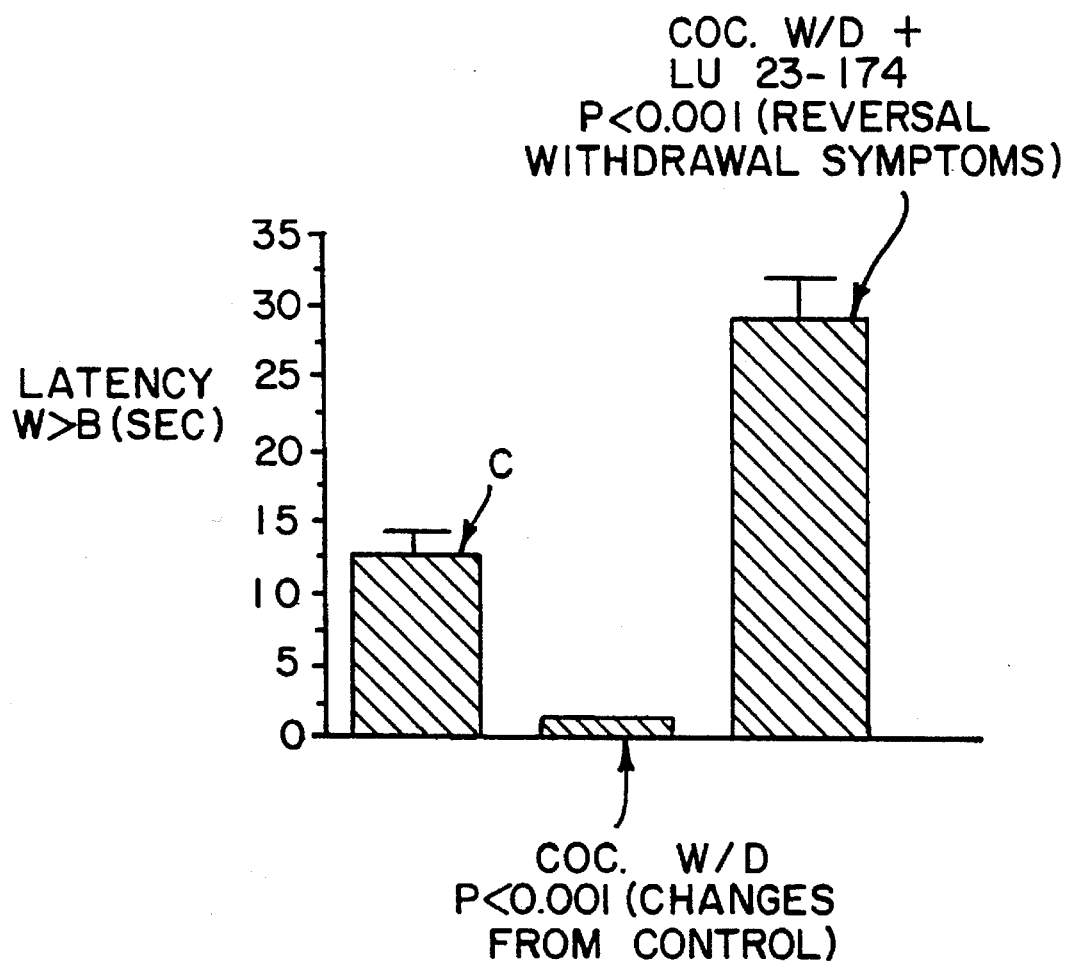
Figure 4A:
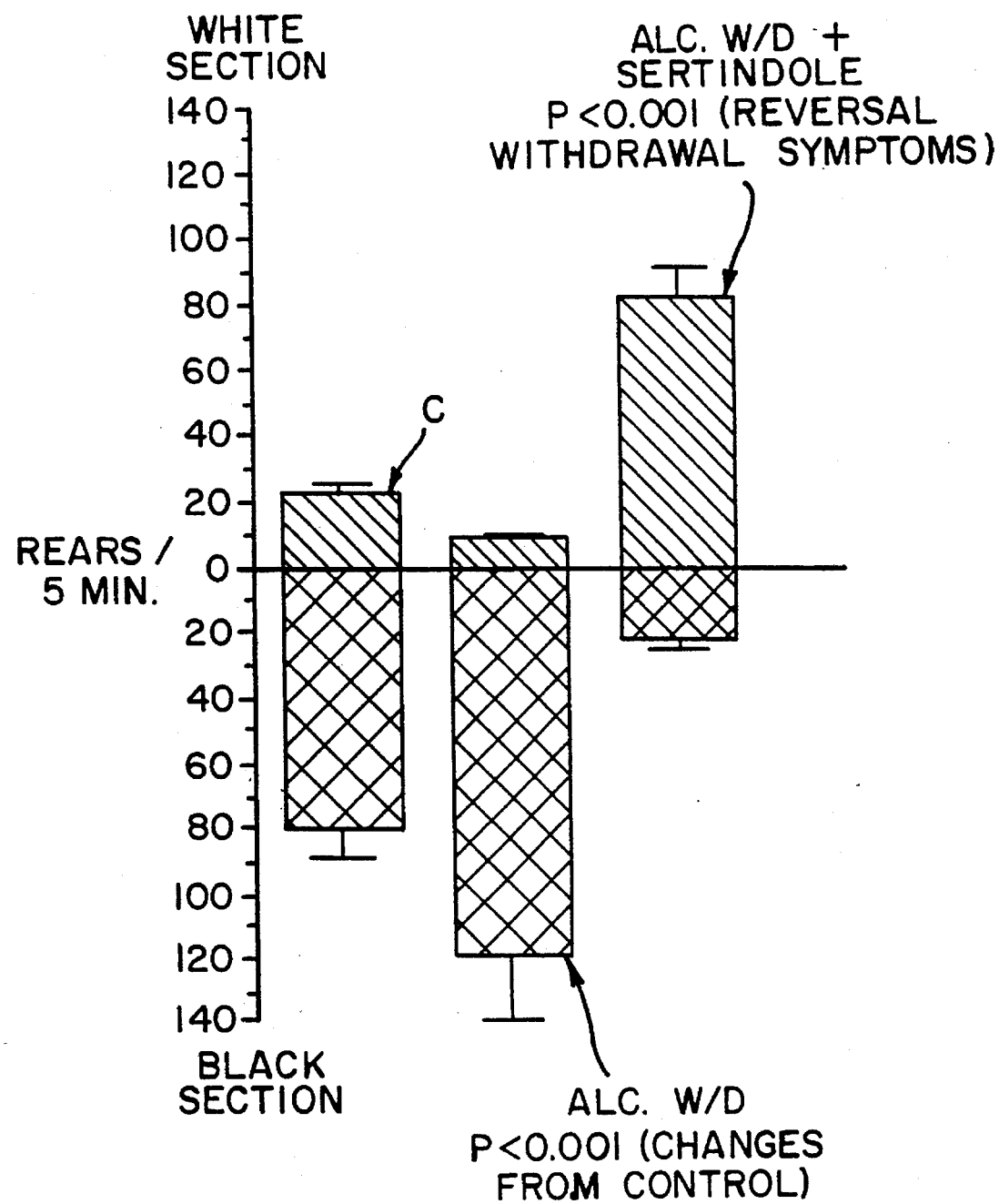
FIGS. 4a–4d illustrate the effect of administration of a compound of the invention, i.e. sertindole in a dose of 0.1 mg/kg i.p., on alcohol withdrawal symptoms.
Figure 4B:
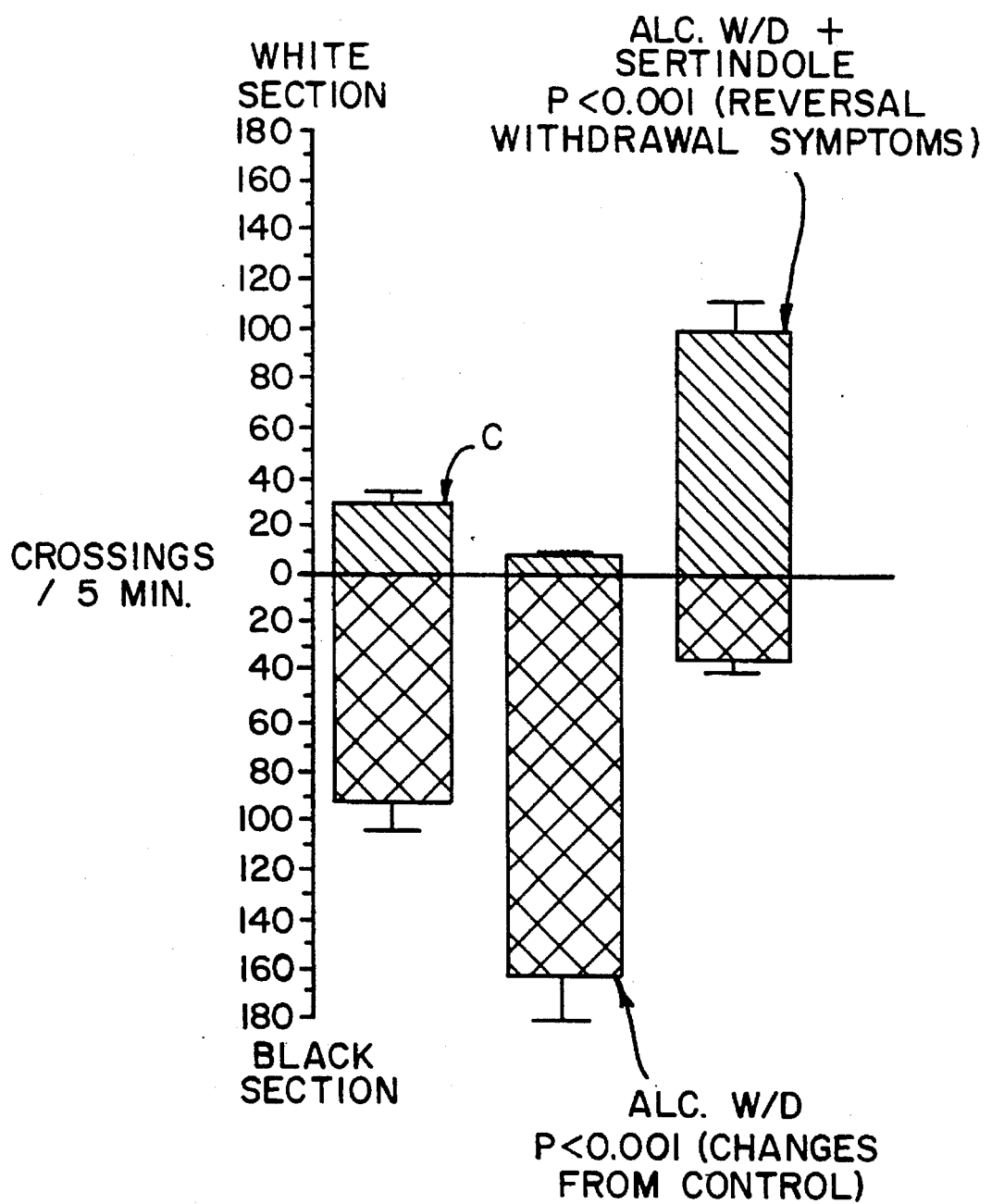
Figure 4C:
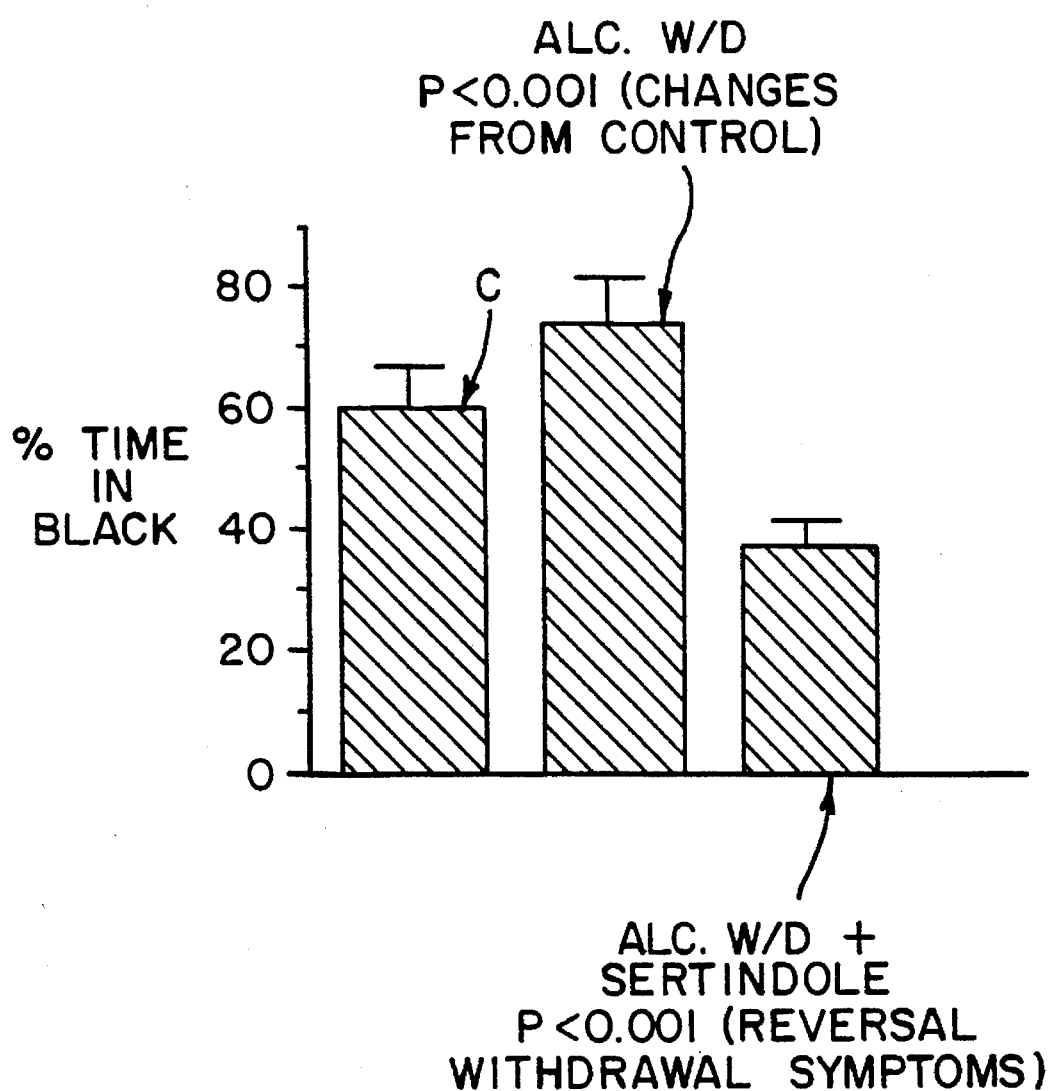
Figure 4D:
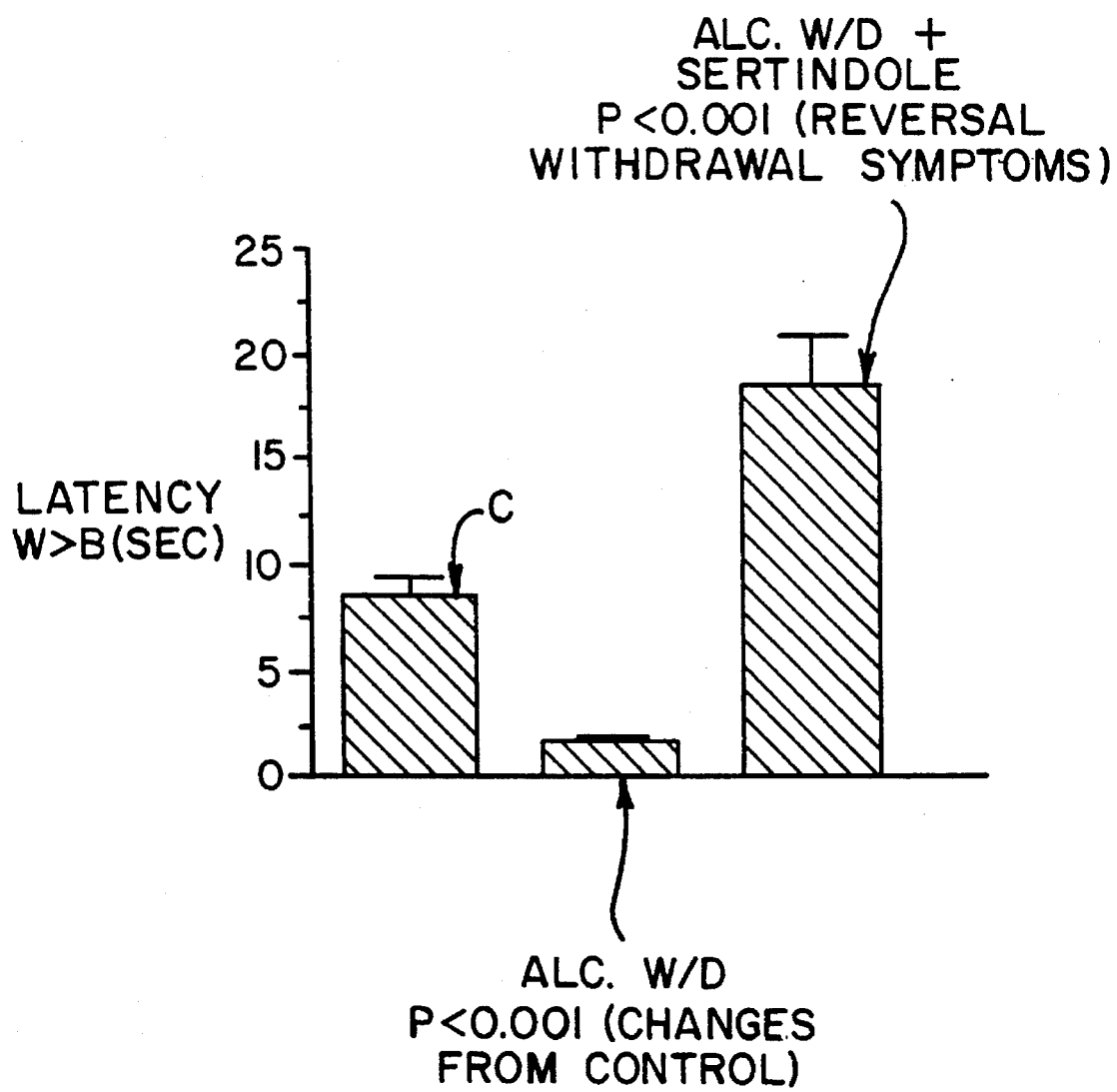

The results are shown graphically in FIG. 2 for one compound according to the invention, i.e. sertindole, administrated in a dose of 0.1 mg/kg.

C) Cocaine Withdrawal

The experimental design was as described for the diazepam withdrawal studies. Cocaine was given (1 mg/kg i.p., b.d) for 14 days and test compound was given during withdrawal for 24 hours (i.p., b.d). The assesment of the behavioural changes was as described for diazepam.

The results are shown graphically in FIG. 3 for one compound according to the invention, i.e. sertindole, administrated in a dose of 0.1 mg/kg.

D) Alcohol Withdrawal

The experimental design was as described for the diazepam withdrawal studies. Alcohol was given for 14 days (8% in drinking water) and withdrawn for 24 hours. Test compound was given during withdrawal (i.p., b.d). The assesment of the behavioural changes was as described for diazepam.

The results are shown graphically in FIG. 4 for one compound according to the invention, i.e. sertindole, administrated in a dose of 0.1 mg/kg.

It appears from Table 1 that the compounds of the invention are without or substantially without cataleptic activity and accordinly being lacking the extrapyramidal side effects probably associated with the corresponding known 3-(1,2,3,6-tetrahydro-4-pyridyl) and 3-(1-piperazinyl) derivatives.

It is clearly demonstrated in FIG. 1 and 2 that the compound according to the invention has a marked relieving effect on the symptoms following to the withdrawal of diazepam and nicotine, respectively. So, the test compound is seen to have a statistically significant inhibiting effect on the withdrawal behavioural changes both as regards diazepam and nicotine.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting maschine. Examples of adjuvants or diluents comprise: corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

1) Tablets containing 0,5 milligrams of sertindole calculated as the free base:

| | |
|---|---|
| Sertindole | 0.5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

2) Tablets containing 1 milligrams of compound No 3 calculated as the free base:

| | |
|---|---|
| Comp. 3 | 1.0 mg |
| Lactose | 16 mg |
| Potato starch | 45 mg |
| Sacc'harose | 106 mg |
| Sorbitol | 6 mg |
| Talcum | 9 mg |
| Gelatine | 4 mg |
| Povidone | 3 mg |
| Magnesium stearate | 0.6 mg |

| 3) Syrup containing per milliliter: | |
| --- | --- |
| Comp. 16 | 5.0 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

| 4) Solution for injection containing per milliliter: | |
| --- | --- |
| Sertindole | 0.2 mg |
| Acetic acid | 17.9 mg |
| Sterile water | ad 1 ml |

| 5) Solution for injection containing per milliliter: | |
| --- | --- |
| Comp. 3 | 0.5 mg |
| Sorbitol | 42.9 mg |
| Acetic acid | 0.63 mg |
| Sodium hydroxide | 22 mg |
| Sterile water | ad 1 ml |

We claim:

1. A method for alleviating, relieving or suppressing the withdrawal symptoms or suppressing the dependency of cocaine, diazepam, morphine, nicotine, alcohol, or amphetamines, comprising administering, an effective amount to a subject, a 1-aryl-3-(4-piperidyl)-indole derivative having the formula:

I wherein $R^1$ is hydrogen, halogen, lower alkyl, lower alkoxy, hydroxy, cyano, nitro, lower alkylthio, trifluoromethyl, trifluoromethylthio, lower alkylsulfonyl, amino, lower alkylamino or lower dialkylamino;

R is phenyl optionally substituted with one or more substituents independently selected from the following: halogen, lower alkyl, lower alkoxy, hydroxy, trifluoromethyl, and cyano; and $R^2$ is hydrogen, cycloalkyl having from three to eight carbon atoms, lower alkyl or lower alkenyl, optionally substituted with one or two hydroxy groups, any hydroxy group present being optionally esterified with an aliphatic carboxylic acid having from two to twenty-four carbon atoms inclusive, or $R^2$ is a group having Formula IV:

IV wherein n is an integer of from 2–6, inclusive;

W is O, S or N—$R^3$, wherein $R^3$ is H, lower alkyl or cycloalkyl having from three to eight carbon atoms;

U is N or CH;

Z is —$(CH_2)_m$—, m being 2 or 3, or Z is —CH=CH— or 1,2-phenylene optionally substituted with halogen or trifluoromethyl, or Z is —$COCH_2$— or —$CSCH_2$—;

V is O, S, $CH_2$, or $NR^4$, wherein $R^4$ is hydrogen, lower alkyl optionally substituted with one or two hydroxy groups, lower alkenyl or a cycloalkylmethyl group, said cycloalkyl having from three to six carbon atoms inclusive;

or a pharmaceutically acceptable acid addition salt thereof;

or a pharmaceutically acceptable acylated prodrugs of free hydroxy or free amino groups.

2. A method according to claim 1, wherein the compound used is a compound of the general Formula I as defined in claim 1 wherein R is phenyl substituted in the 4 position with fluoro, or R is 2- or 3-thienyl;

$R^1$ is hydrogen, halogen, lower alkyl, lower alkoxy, cyano, trifluoromethyl, or lower alkylsulphonyl;

$R^2$ is a group having the Formula IV as defined in the foregoing wherein n=2–6;

W is O or S;

U is N;

Z is —$(CH_2)_2$—, —$(CH_2)_3$—, or —CH=CH; and

V is O, $CH_2$ or $NR^4$, $R^4$ being hydrogen or lower alkyl;

or a pharmaceutically acceptable acid addition salt thereof or prodrug therefor.

3. A method according to claim 1, wherein a compound used is a compound having formula:

of a pharmaceutically acceptable acid addition salt thereof or a prodrug therefor.

* * * * *